United States Patent [19]

Vickroy et al.

[11] Patent Number: 4,998,921
[45] Date of Patent: Mar. 12, 1991

[54] INTERMITTENT I.V. THERAPY NEEDLE SHEATH

[76] Inventors: Harold C. Vickroy, 1980 Liliano Dr., Sierra Madre, Calif. 91024; Nancy Zera, P.O. Box 43, Campbell, Calif. 95009

[21] Appl. No.: 439,105
[22] Filed: Nov. 20, 1989
[51] Int. Cl.⁵ ............................................. A61M 5/178
[52] U.S. Cl. .................................... 604/167; 604/192; 604/411
[58] Field of Search ............... 604/283, 411, 198, 263, 604/905, 167, 414, 86, 87, 243, 413, 244, 171, 187, 192

[56] References Cited

U.S. PATENT DOCUMENTS

| | | |
|---|---|---|
| 2,674,246 | 4/1954 | Bower . |
| 3,134,380 | 5/1964 | Armao . |
| 3,354,881 | 11/1967 | Bloch . |
| 4,139,009 | 2/1979 | Alvarez . |
| 4,564,054 | 1/1986 | Gustavsson . |
| 4,725,267 | 2/1988 | Vaillan court . |
| 4,735,618 | 4/1988 | Hagen . |
| 4,775,369 | 10/1988 | Schwartz . |

Primary Examiner—John D. Yasko

[57] ABSTRACT

The invention provides a protective sheath for an intermittent I.V. therapy needle to protect medical personnel against accidental self puncture while performing intermittent I.V. therapy. The sheath is a flexible transparent plastic tube having an internal septum which provides two separate interior compartments. One compartment is adapted to house a needle and a portion of the needle hub, providing an enclosed sterile environment when the device is attached to the needle assemblage of a secondary medication source. The second compartment is adapted to be releasably affixed to the exterior of an eccess port at a Y-site located on intravenous tubing used for intermittent I.V. therapy. The walls of the sheath fold and compress as the needle is advanced through the internal septum into the Y-site where the contents of the secondary medication source are infused into the I.V. tube main line through the Y-site. Upon removal of the needle from the Y-site, the septum reseals and the tubular wall of the sheath through material resilience assume the original elongated shape. A pull is required to release the attachment end of the sheath from the Y-site port which also helps straighten out the sheath tube. When sufficient pull is exerted to release the sheath from the Y-site head, the needle is fulley encased in the needle housing preventing premature exposure. The encased needle can be safely disposed of or, in some cases, reused on the same patient with the same medication. The device is also useful with syringes.

1 Claim, 5 Drawing Sheets

INTERMITTENT I.V. THERAPY NEEDLE SHEATH

BACKGROUND OF THE INVENTION

1. Field of the Invention

This invention relates to medical equipment used for the infusion of medications into an intravenous therapy system. More precisely, the invention is a protective sheath for the needle portion of a needle assemblage which is used to inject medication into the Y-site on intravenous tubing during intermittent I.V. therapy. The sheath protects the medical worker from accidental puncture by the intermittent I.V. therapy needle before and especially after the injection of the medication.

2. Description of the Prior Art

Intermittent intravascular injection therapy usually referred to as I.V. therapy is commonly used in hospitals and emergency situations requiring intravascular injection of medications to sustain life and for direct intravascular injection of medications into patients requiring this therapy. Intermittent I.V. therapy needles in use today are disposable units provided in prepackaged sterile containers. Each needle is commonly housed in a full covering rigid plastic cap which must be removed prior to use. After an intermittent I.V. therapy needle has been used, nursing procedure in effect today requires it to be properly disposed of in disposal containers supplied in every patient's room. It is primarily during this stage of the procedure where medical personnel often inadvertently puncture themselves with the used needle. This would not be of particular concern were the patient not infected with some form of contagious disease. The fairly recent occurrence of the disease acquired immune deficiency syndrome, AIDS for short, has now made many medical procedures, especially those involving contact with body fluids of the infected patient, a major concern to medical workers. Intravenous or I.V. therapy systems appear to offer little or no threat to the nurse or technician administrating the therapy. This is not necessarily true because these systems do create a passageway from the patient's circulatory system directly to the I.V. tubing and to the medication injection Y-site port. The potential exists for contamination especially if blood backup occurs within the tubing. Care against accidental self puncture must be exercised by both the nurse and the technician even when a Y-site application is used.

For examination of past art, a patent search was conducted directed towards devices involving protective sheaths for hypodermic needles and particularly for needle protective coverings useful in intravenous therapy systems. Although no protective sheaths particularly for I.V. needle assemblages were seen in patents examined, the following patented devices appeared most pertinent to our invention:

Bower was granted U.S. Pat. No. 2,674,246, dated Apr. 6, 1954, for a rigid open-ended sheath designed to apply pressure to the site of injection to lessen the shock of hypodermic needle penetration to the patient.

Armao was issued U.S. Pat. No. 3,134,380, on May 26, 1964, for an open-ended hypodermic needle which serves to shield the needle from the patients view to avoid alarm.

On Feb. 13, 1979, Alvarez was granted U.S. Pat. No. 4,139,009, for a hypodermic needle assembly with a retractable needle cover. The cover consists of resilient bars which open sideways when compressed, exposing the needle shaft.

U.S. patents issued to Schwartz, U.S. Pat. No. 4,775,369; to Hagen, U.S. Pat. No. 4,735,618; and to Vaillancourt, U.S. Pat. No. 4,725,267, all show collapsible plastic or foam sheaths having apertured distal ends for passage of hypodermic needles.

The U.S. patent issued to Bloch, U.S. Pat. No. 3,354,881, teaches a detachable hypodermic needle protector consisting of a closed ended flexible walled tube containing a chemical guard medium. Both closed ends are self-sealing septums, one end of which the needle is passed through to house the distal end of the needle within the chemical medium. In use, the needle protector is compressed, for example, against the patient's skin forcing the needle through the second septum. Upon removal of the needle from the patient, the needle protector resumes the original shape and the needle is withdrawn back inside, to be chemically treated and reused. This device would not be useful for intermittent I.V. therapy systems.

The Gustavsson device, U.S. Pat. No. 4,564,054, dated Jan. 14, 1986, shows a fluid transfer system having a two piece detachable protective sheath for preventing air contamination when transferring a liquid substance from one vessel to another.

All of the past art devices, excluding the Bloch and Gustavsson patents, show sheaths which provide some measure of structural protection for the needle but contain various apertures or openings which do not maintain the needle in a sterilized environment. This necessitates providing a second protective covering or other means to maintain a sterilized needle. This second protective covering would not only add bulk to the device but would be cumbersome to handle, and would increase the final cost of the unit.

None of the past art devices seen are structured specifically as intermittent I.V. therapy needle sheathes for needles in needle assemblages used at I.V. Y-site ports for medication infusion during intermittent I.V. therapy.

SUMMARY OF THE INVENTION

Therefore, in practicing our invention, we have provided a sheath which is permanently attached to a intermittent I.V. therapy needle hub with the needle completely encased in a sterile tubular covering. Our sheath is particularly designed for the needle in the needle assemblage used at a Y-site port during intermittent I.V. therapy. The device is especially directed towards protecting the attendant from accidentally puncturing herself or himself with the needle and being contaminated by potentially infectious residue contained in or on the used needle. Our sheath can be used with a disposable needle which is disposed of after a single use or with a needle to be reused during intermittent IV therapy on the same patient. The sheath according to the invention is a small elongated transparent plastic tube. The wall of the plastic tube is thin-wall and flexible. Although amber coloring is preferred, the plastic may be of any color so long as sufficient transparency is maintained to view enclosures inside the tube. The tube has two open ends. One open end is sealed around the hub of a hypodermic needle with the needle inside the tube. The other open end has an inwardly flanged attachment lip. A septum in the form of a disc membrane divides the tube into two compartments and seals off the needle end from the attachment lip end providing a sterile sealed compartment for the needle. The septum is located more towards the open attachment lip end of the sheath, leaving a larger compartment housing the needle. The second smaller compartment is adapted for releasable connection over the head of the angled member or port at the Y-site on an intravenous tubing system. The sheath of the immediate invention, permanently attached to the hubs of variably sized pre-sterilized hypodermic needles with the needles encased, can either be provided in one particular size or in a variety of sizes for use selection by hospital staff. Once attached to a sterile intermittent I.V. therapy needle and to the I.V. needle assemblage, the sheath will maintain the needle in a sterilized condition as the needle and needle hub is completely enclosed.

The Y-site of an intravenous therapy system is similar to a short T-connector. A port in the form of an angled stub accessing the tubing of the primary I.V. line has a resealing membrane through which medications can be injected by needle into a flowing I.V. line. The medication will then pass down the tubing with the other I.V. solutions which flow from I.V. bottles positioned above the Y-site. The medication and solution will pass through a catheter inserted directly into the patient's vein. To administer the medication using the preferred embodiment of the invention, the assembled sheath and needle with the needle attached by tube to the unit containing a specified amount of medication is positioned over the stub end or port of the Y-site attachment on the I.V. tubing. The stub end of the Y-site is usually referred to as the port. The sheath is then snapped over the Y-site port and the needle advanced and inserted through the sheath septum and then through the Y-site septum. The sides of the flexible sheath fold and compress as the needle is advanced. The contents of the medication container can then be allowed to flow into the lumen or port tube at the Y-site. When the needle is retracted both the head septum and the interior sheath septum reseal as the needle is pulled into the needle housing. The open attachment lip end of the sheath tube pressured against the Y-site port holds temporarily and helps pull the flexible sides of the sheath tube longitudinally back into the original elongated tubular shape as the needle is being pulled out of the Y-site port. The attachment lip open end of the sheath tube remains connected to the Y-site head until removed with a slight tug. The needle has therefore remained covered but visible through the transparent plastic during the entire procedure. In this manner, the attendant is protected from exposure to the needle point during the procedure and after the needle is withdrawn. If the needle is not to be used again on the same patient, the entire sheath with encased needle sealed inside can be safely disposed of.

Therefore, it is a primary object of our invention to provide an intermittent I.V. therapy needle sheath which protects medical personnel from accidental puncture or exposure to potentially infectious agents during injections of secondary medications to patients on intermittent I.V. therapy.

A further object of our invention is to provide a an intermittent I.V. therapy needle sheath which is permanently attached to the needle hub, maintaining the needle inside in a sterilized condition, and which allows the needle to be used on a Y-site port during intermittent I.V. therapy without removing the protective sheath from the needle.

An even further object of our invention is to provide an intermittent I.V. therapy needle sheath which is itself structured as a single unit and can be either molded onto the needle hub during manufacture or permanently affixed later.

A still further object of our invention is to provide an intermittent I.V. therapy needle sheath which is inexpensive to produce, and requires little or no assembly.

An even further object of our invention is to provide an intermittent I.V. therapy needle sheath which is transparent so viewing of the needle tip is possible during the procedure.

Further objects and advantages of our invention will become apparent from studying described and numbered parts detailed in the remaining specification with subsequent comparison of the numbered parts described with like numbered parts illustrated in the appended drawings.

DESCRIPTION OF THE PREFERRED EMBODIMENT

Figure 1:
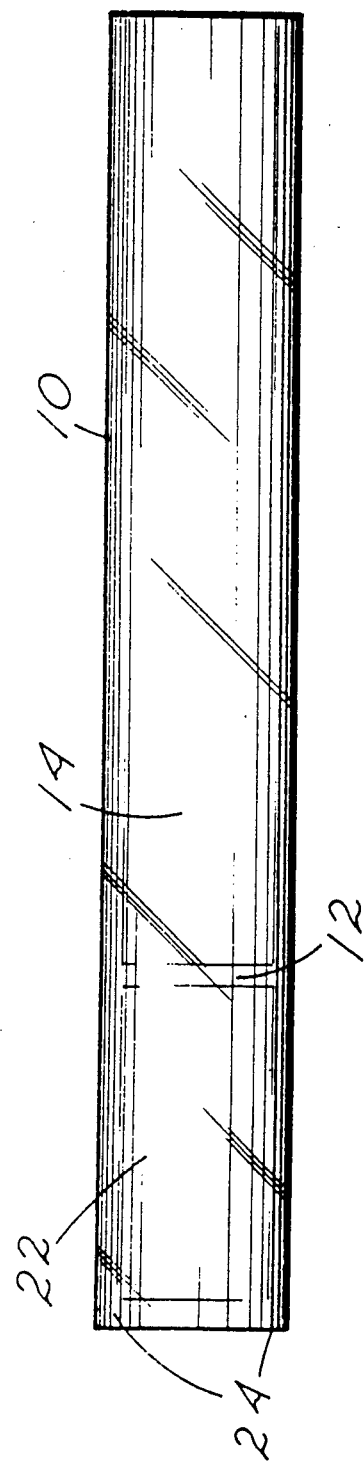
FIG. 1 is a side view of the intermittent I.V. therapy needle sheath according to the invention illustrating the transparent plastic structure of the tube.
Figure 2:
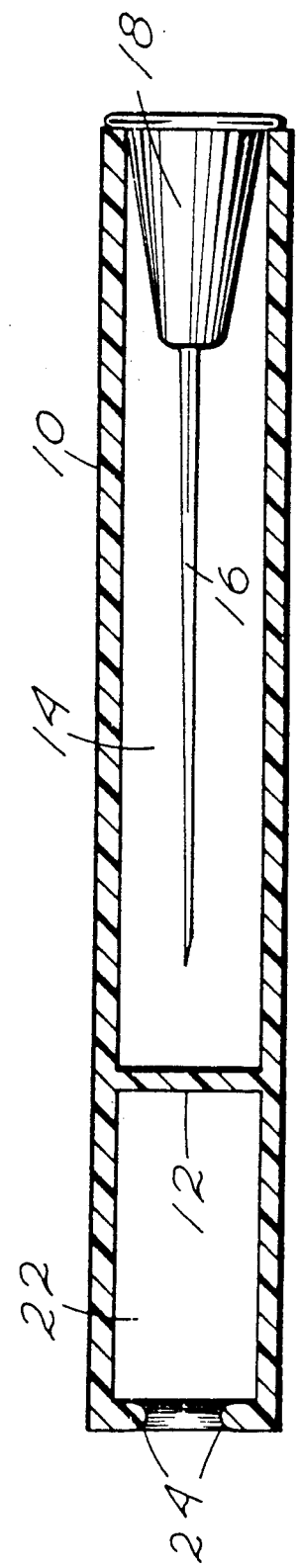
FIG. 2 is a cross-sectional side view of the sheath showing an intermittent I.V. therapy needle encased in a needle compartment formed right in the illustration by a dividing septum leaving a smaller Y-site adaptor compartment shown on the left.
Figure 3:
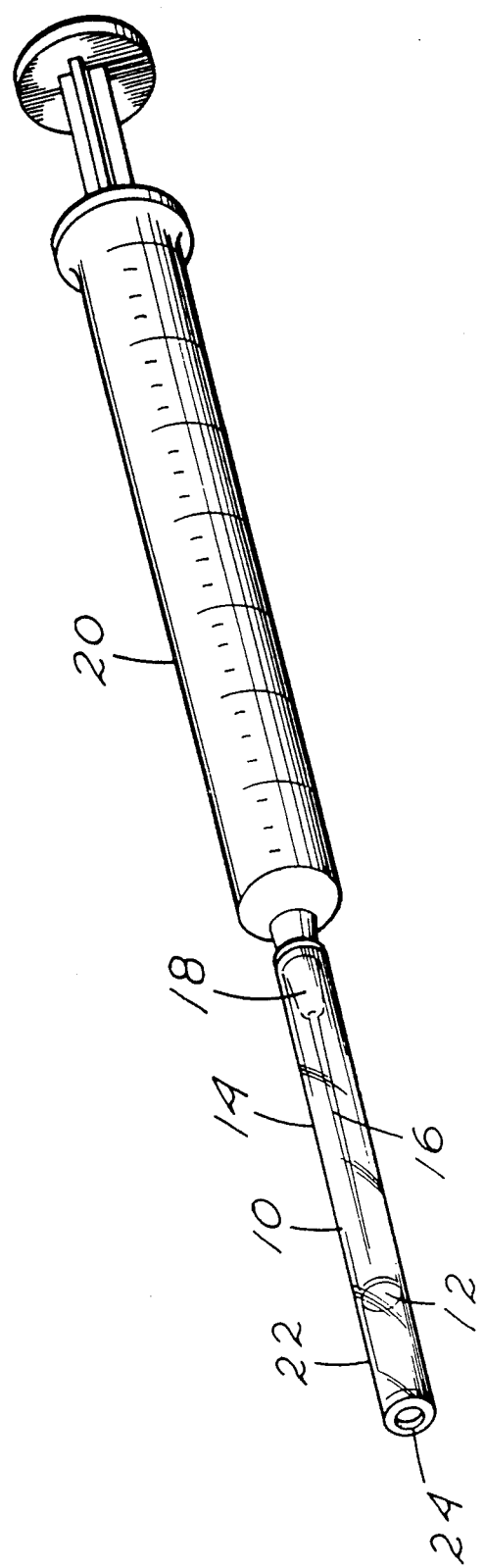
FIG. 3 is a perspective view of the assembled needle and sheath illustrating a second use with the sheath affixed to a syringe for emergency injection of a medication at the Y-site port.
Figure 4:
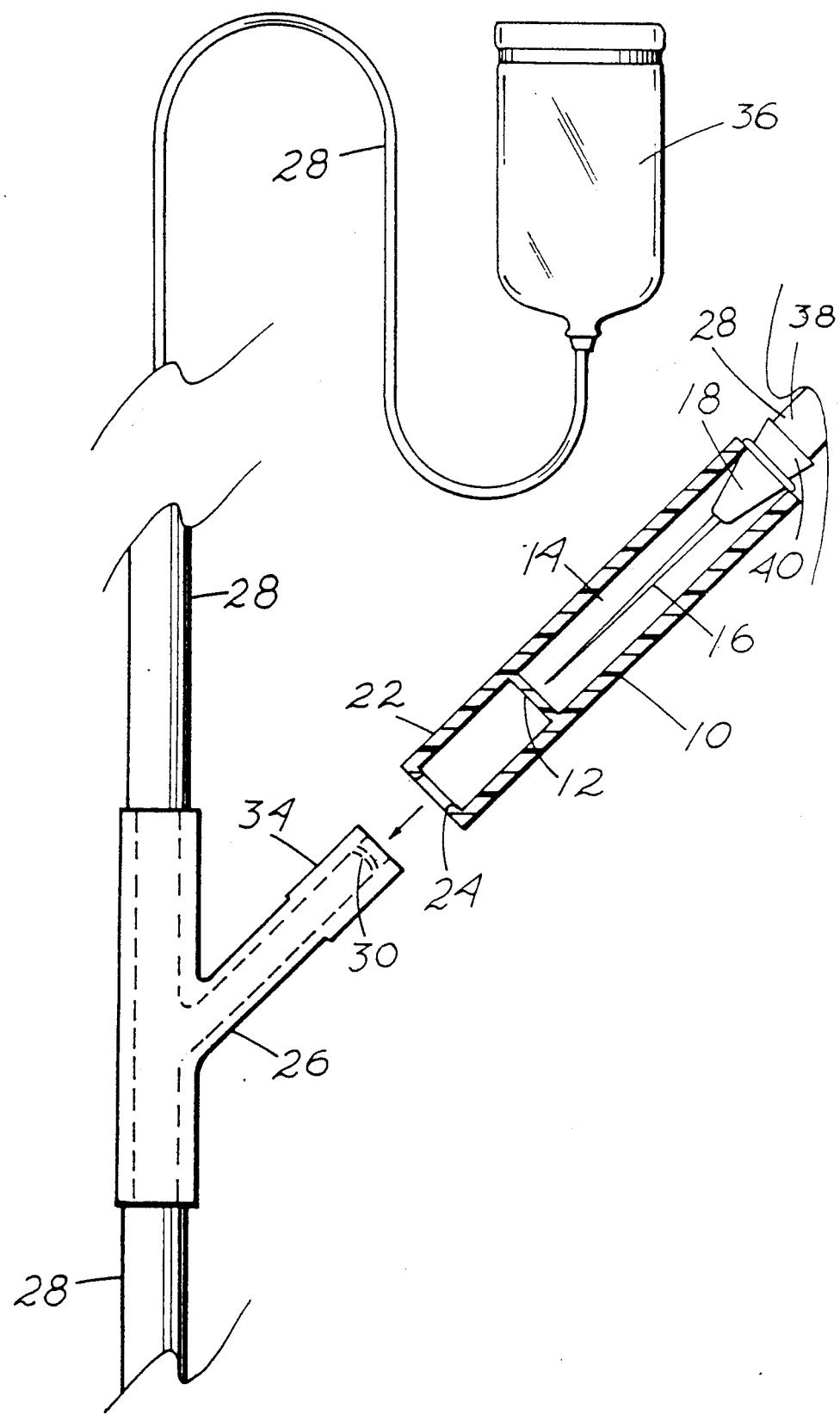
FIG. 4 is an in-use illustration depicting the intermittent I.V. therapy needle encased in the sheath with the sheath affixed to a medication input source and the sheath shown cross-sectioned and positioned for connection to the port stub at the Y-site of an intravenous tubing system.

In the drawings, the present invention which provides a protective sheath 10 for an intermittent I.V. therapy needle 16 to protect medical personnel against accidental self puncture while performing intermittent I.V. therapy is illustrated in a side view in FIG. 1 and sectioned for inside disclosure in FIG. 2. Sheath 10 is designed for sanitary encasement of needles 16 used for intermittent intravenous therapy which is medically referred to as intermittent I.V. therapy. As can be seen in the drawings, sheath 10 is an elongated open ended hollow tube comprised of a flexible resilient transparent plastic. Elastomeric silicone is the suggested material of manufacture for sheath 10, although any suitable material having similar characteristics is also acceptable. Located adjacent one opened end of sheath 10 is an internal septum 12, which seals the interior lumen and creates two un-equally sized separate compartments. See FIG. 2. The larger compartment, referred to as needle housing 14, is sized for encasing an intermittent I.V. therapy needle, needle 16, and for sealed attachment to needle hub 18. Sheath 10 is permanently attached to needle hub 18, either molded around needle hub 18 during the manufacturing process or attached later by adhesive attachment, ultra-violet sealing, ultrasonic bonding, or by other suitable methods. Needle housing 14 is a completely enclosed air tight compartment except for the internal fluid passageway or bore of needle 16. Needle hub 18 is the hub of variously sized available intermittent I.V. therapy needles 16 and can be comprised of metal, plastic or a combination thereof. A portion of needle hub 18 projects beyond the end of sheath 10 and is adapted for attachment to needle assemblage 40 and to syringe 20. See the perspective view at FIG. 3 and the use view at FIG. 4. The smaller second compartment of sheath 10 is referred to as Y-site adaptor 22. The open end of Y-site adaptor 22 is rimmed with an over hanging edge, attachment lip 24, which helps to retain sheath 10 onto the widened head portion of port 34 at Y-site 26 attached to I.V. tubing 28. As illustrated in FIG. 4, Y-site 26, shown enlarged, is a medical fluid infusion site situated below medication container 36 along I.V. tubing 28, shown reduced, having an angled head member, port 34, with resealable membrane 30, a septum similar to spectum 12, blocking the distal end. The port 34 septum, resealable membrane 30 allows infusion of fluid medication 32 from a medication source 38 through the bore in needle 16 into the I.V. system at Y-site 26. Prior to use, sheath 10 with needle 16 sealed inside is provided prepackaged fully covered in a pre-sterilized container. Once removed from the sterilized container, needle hub 18 is attached to a compatible needle assemblage 40 affixed to an end of an I.V. tubing 28 connected to a medication source 38. Needle assemblage 40 is usually either a threaded or a snap-on connection. The interior of needle hub 18 is therefore adapted with threads, a snap-on sealing ring, or any releasable connection. Once needle hub 18 is affixed to needle assemblage 40, using a known aseptic technique, needle 16 will still remain sterile within sheath 10. This is also the case when needle hub 18 is attached to syringe 20 as illustrated in FIG. 3.

Figures 5, 6:
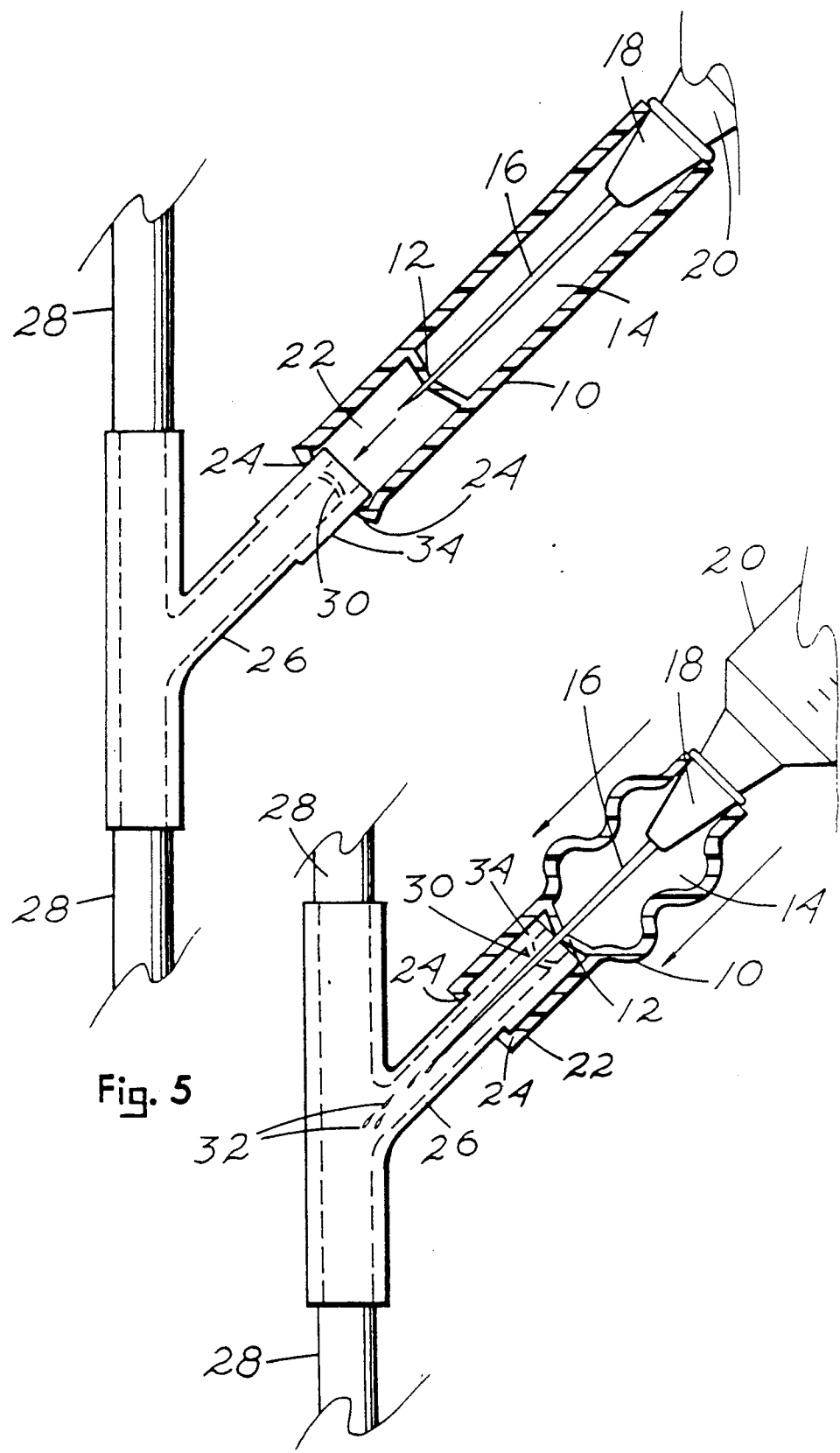
FIG. 5 is a cross sectioned view of the sheath with the needle encased showing the Y-site adaptor end of the needle sheath partially inserted over the head of the Y-site access port with the needle piercing the inner septum of the sheath tube.
FIG. 6 shows the sheath in a cross sectioned view with the Y-site adaptor end of the sheath completely attached over the head of the Y-site port, the side wall of the sheath compressed, and the needle in the process of injecting medication into the lumen or port at the Y-site head.
Figure 7:
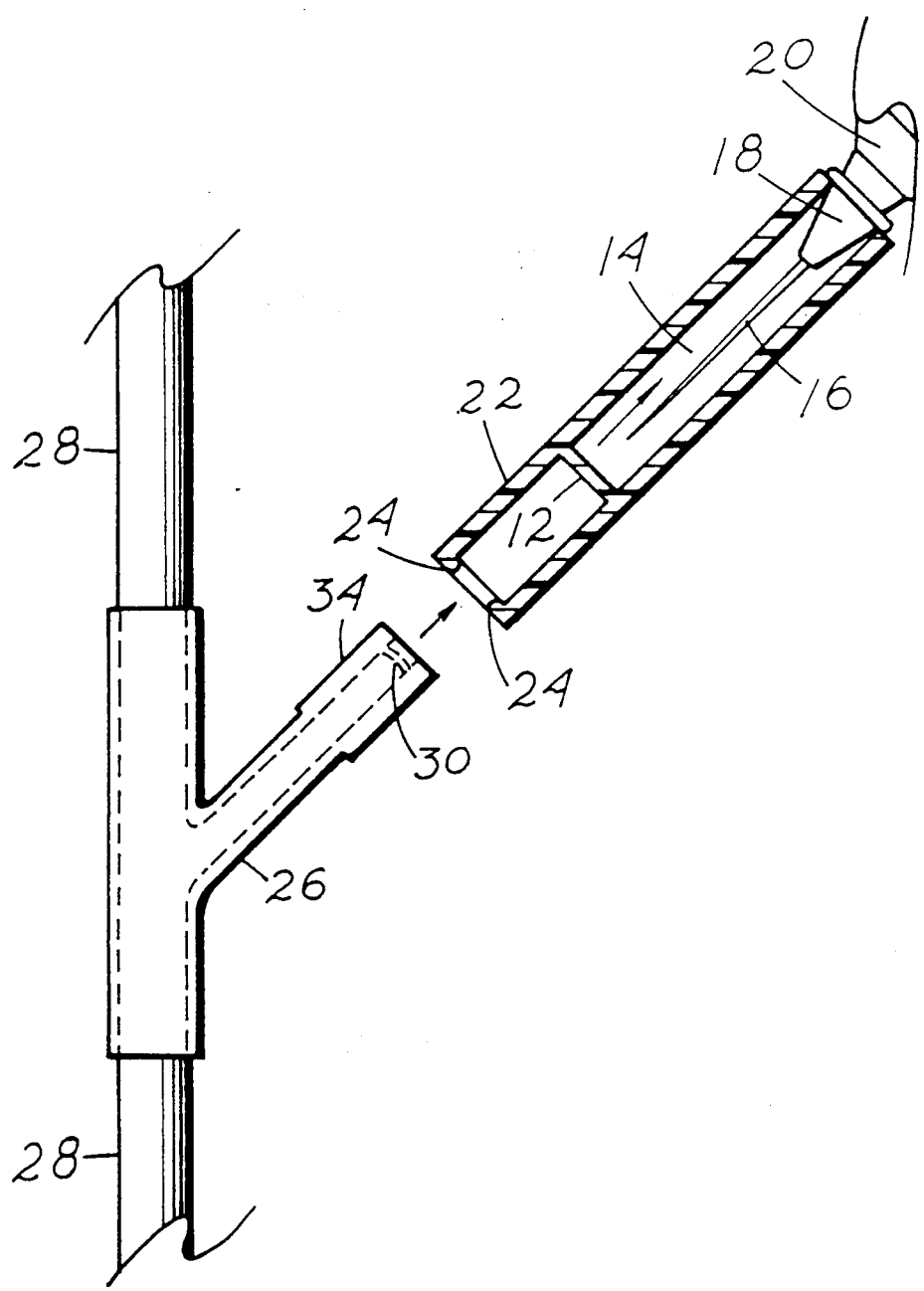
FIG. 7 shows the sheath in a cross sectioned view after withdrawal of the needle from the head of the Y-site port illustrating the needle fully encased back in the needle compartment with the septum self-sealed and the sheath tube longitudinally restored. The needle is illustrated ready for disposal or reuse for medicating the same patient.

To infuse medication 32 by injection or drip method into I.V. tubing 28, the distal end of sheath 10 is positioned over port 34 at Y-site 26 as illustrated in FIG. 4 and FIG. 5. Y-site adaptor 22 is forced over port 34 at Y-site 26 until attachment lip 24 slips over the back edge of the widened head section of port 34. See FIG. 6. Needle 16 is then advanced towards Y-site 26, passing through septum 12 and resealable membrane 30 into the lumen of Y-site 26. The tubular wall of sheath 10 folds and compresses as needle 16 is advanced. As FIG. 6 shows, medication 32 can then be released from medication source 38 into the interior of I.V. tubing 28 through needle 16. After medication 32 injection, as needle 16 is withdrawn, resealable membrane 30 and septum 12 automatically reseal the puncture sites created by needle 16. The exterior tubular wall of sheath 10 returns to the original shape due to the natural resilience nature and elasticity of the plastic material. Y-site adaptor 22 remains temporarily affixed onto the head section of port 34 at Y-site 26 until manually removed with a slight tug. This prevents the connection from slipping off prematurely and exposing needle 16. The pulling also helps return the compressed wall of sheath 10 to the original tube shape. The withdrawn sheath 10 with used needle 16 inside, shown in FIG. 7, can be disposed of or the assembled sheath 10 with needle 16 can be attached to needle assemblage 40 and reused on the same patient for intermittent injection of the same medication 32 for a limited time. It is recommended, however, that sheath 10 with used needle 16 sealed inside be disposed of properly after the first use.

Any nurse or health care worker using needle 16 encased in sheath 10 is protected from inadvertent puncture by needle 16 throughout the entire intermittent I.V. therapy medication infusion procedure. The used device, sheath 10 with used needle 16 inside, can be safely disposed of without fear of exposure. This invention can also conceivably be used to safely obtain urine samples from an in-dwelling urinary catheter as a similar type of Y-site 26 is usually used on these devices. In this instance, sheath 10 could be used with syringe 20 as illustrated in FIG. 3. Sheath 10 would safely prevent any leakage of the obtained sample from needle 16. Sheath 10 with needle 16 encased could also be used with syringe 20, FIG. 7, for safe injection of emergency medication into Y-site 26 through port 34 if needed.

While the present invention has been described and illustrated with respect to a specific embodiment, it is obvious that numerous variations are possible by those skilled in the art. Therefore, this disclosure is to be considered illustrative only of the inventive theory involved with modifications limited only by the scope of the appended claims.

What I claim as my invention:

1. A tubular sheath encasing an I.V. therapy needle with attached needle hub, comprising an elongated single annular wall forming a tubular member, said tubular member having a first end and an oppositely disposed second end, said tubular member having an attached internally positioned septum dividing said tubular member into one longer compartment and one shorter compartment, said septum structured of sufficiently soft material to allow puncturing thereof by said I.V. therapy needle, said soft material of said septum further being sufficiently resilient to seal a puncture made therein by said I.V. therapy needle upon withdrawal of said I.V. therapy needle therefrom, said needle hub attached within said longer compartment at said second end of said tubular member, one end of said needle hub positioned adjacent said second end of said tubular member so as to allow attachment of a syringe to said needle hub, said I.V. therapy needle extending from one end of said needle hub toward said septum, and terminating adjacent said septum within said longer compartment, said first end of said tubular member being an open end in communication with said shorter compartment, said tubular member having an interior annular lip affixed adjacent said first end, said tubular member structured of material being sufficiently flexible to allow said tubular member to be longitudinally collapsible, said I.V. therapy needle positioned within said longer compartment to puncture said septum and enter said shorter compartment upon longitudinal collapsing of said tubular member, said tubular member structured of said material further being sufficiently resilient to automatically resume an elongated original position after collapsing thereof and release of the collapsing pressure thereby retracting said I.V. therapy needle back into said longer compartment, said material structuring said tubular member further being transparent to allow viewing of said I.V. therapy needle and said septum therethrough.

* * * * *